(12) United States Patent
Henderson

(10) Patent No.: US 8,617,207 B1
(45) Date of Patent: Dec. 31, 2013

(54) SURGICAL NEEDLE WITH JAM CLEAT

(75) Inventor: Eric Ross Henderson, Tampa, FL (US)

(73) Assignee: University of South Florida, Tampa, FL (US)

( * ) Notice: Subject to any disclaimer, the term of this patent is extended or adjusted under 35 U.S.C. 154(b) by 321 days.

(21) Appl. No.: 13/107,464

(22) Filed: May 13, 2011

Related U.S. Application Data

(60) Provisional application No. 61/334,862, filed on May 14, 2010.

(51) Int. Cl.
*A61B 17/06* (2006.01)

(52) U.S. Cl.
USPC ........................................................ 606/227

(58) Field of Classification Search
USPC ................................................ 606/222–227
See application file for complete search history.

(56) References Cited

U.S. PATENT DOCUMENTS

| | | | | |
|---|---|---|---|---|
| 1,801,691 | A | * | 4/1931 | Ripper ............................... 163/5 |
| 3,701,461 | A | * | 10/1972 | Bailly et al. ................... 223/102 |
| 3,799,169 | A | * | 3/1974 | Beroff et al. ................... 606/224 |
| 4,932,963 | A | * | 6/1990 | Ritter et al. .................... 606/224 |
| 4,957,502 | A | * | 9/1990 | Takase ............................ 606/223 |
| 6,019,781 | A | * | 2/2000 | Worland ......................... 606/222 |
| 2005/0240203 | A1 | | 10/2005 | Fuseri et al. |
| 2006/0271105 | A1 | | 11/2006 | Foerster et al. |

* cited by examiner

*Primary Examiner* — Melanie Tyson
(74) *Attorney, Agent, or Firm* — Nilay J. Choksi; Jeremy Spier; Smith & Hopen, P.A.

(57) ABSTRACT

A surgical needle including a jam cleat for preventing slippage of suture. The jam cleat includes a suture engaging V-shaped tapered groove having opposing side walls that meet at a jam point.

5 Claims, 6 Drawing Sheets

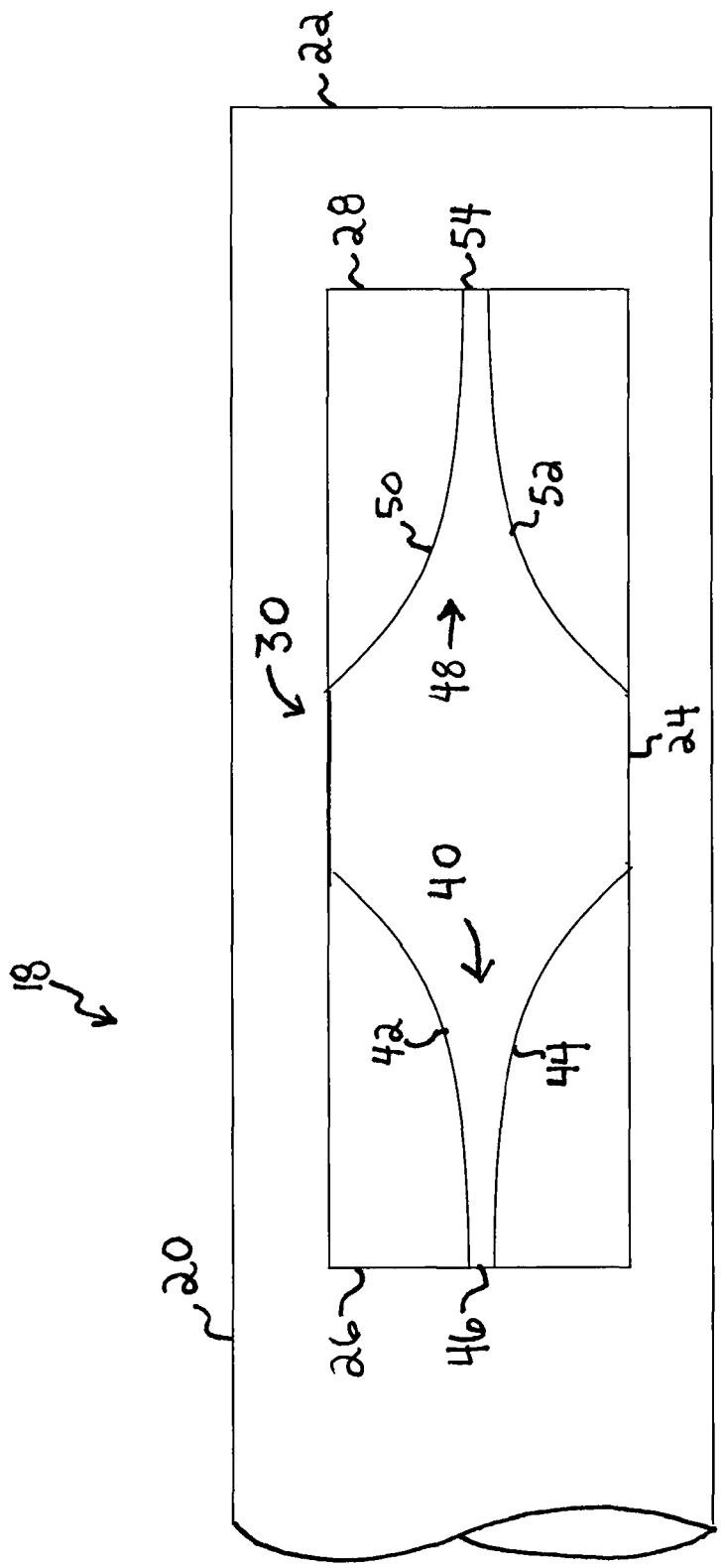

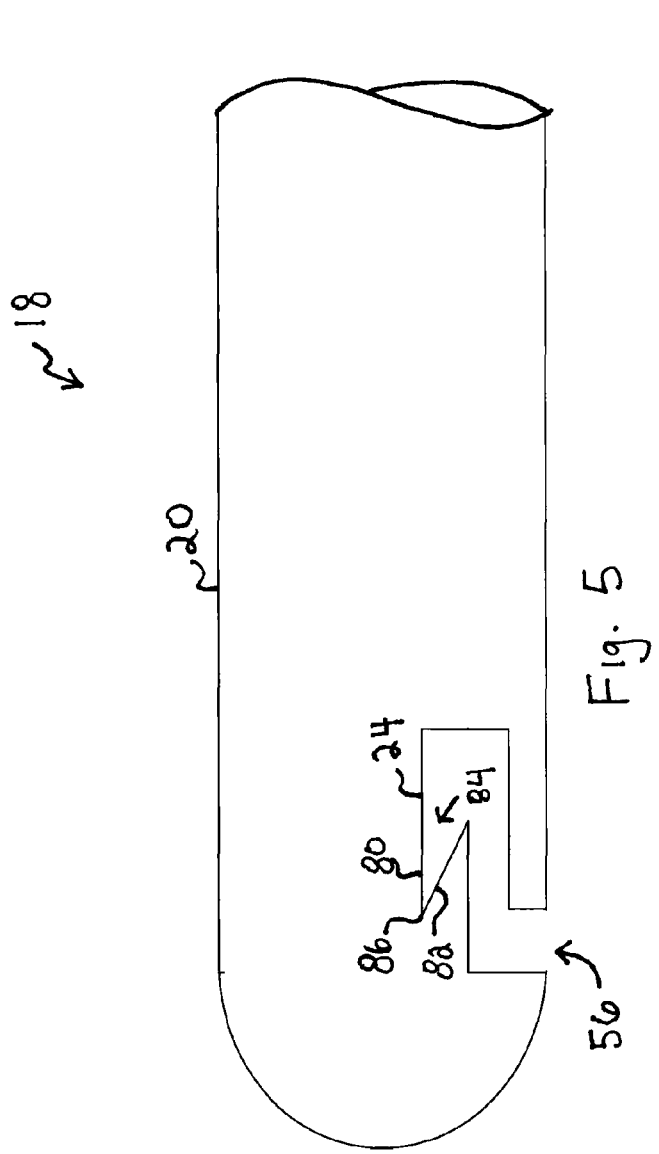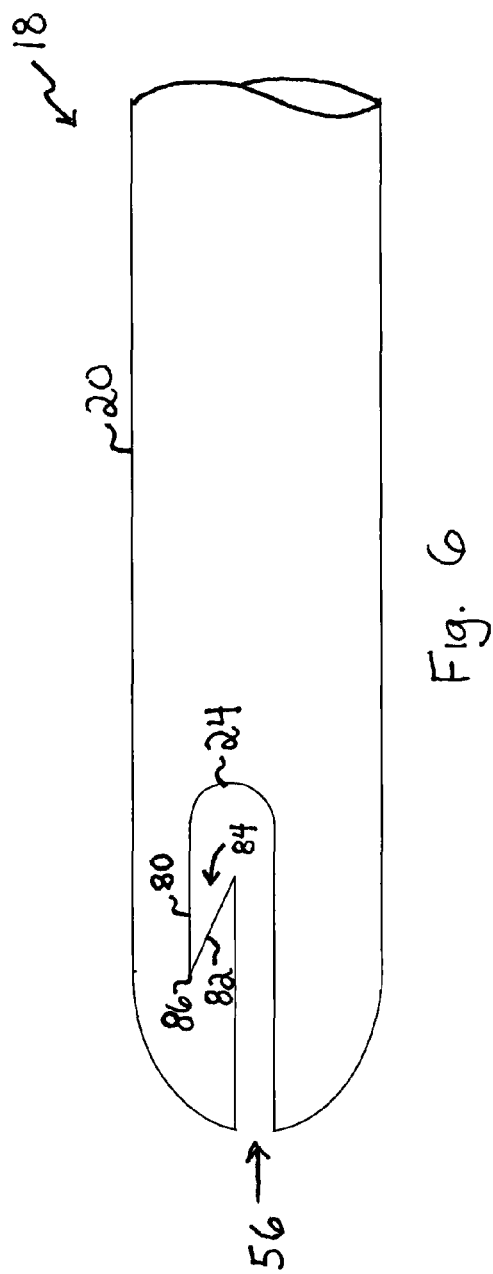

SURGICAL NEEDLE WITH JAM CLEAT

CROSS REFERENCE TO RELATED APPLICATION

This application claims priority to U.S. Prov. Pat. Appl. No. 61/334,862, entitled "FREE NEEDLE WITH JAM CLEAT," filed on May 14, 2010, the contents of which are hereby incorporated by reference.

BACKGROUND OF THE INVENTION

1. Field of the Invention

This invention relates to surgical needles. More specifically, it relates to a surgical needle including a jam cleat for preventing slippage of suture.

2. Description of the Related Art

Suture is used in all aspects of surgery, including tying off blood vessels, wound closure, and repairing injured tissue (tendons, ligaments, muscle, etc.). Suture is commonly manufactured with an attached needle that is used to pass suture through tissue. Often, however, surgeons use suture that is not pre-attached to needles. These sutures, commonly called "ties," may be used without a needle or combined with a needle that has no attached suture, commonly referred to as a free needle. Free needles may also be used to continue sewing a piece of suture that has broken or become detached.

Free needles include an opening (or eye) through which suture passes. The eye is generally oval-shaped with no mechanism to lock suture in place, allowing suture to escape with little force. This generally results in frustration for the surgeon and operative staff alike. What is needed is a quick and secure device for securing suture within the eye of a free needle. However, in view of the prior art considered as a whole at the time the present invention was made, it was not obvious to those of ordinary skill in the art how the limitations of the art could be overcome.

SUMMARY OF THE INVENTION

The long-standing but heretofore unfulfilled need for a quick and secure surgical needle for securing suture is now met by a new, useful, and nonobvious invention. Generally, the surgical needle is a modification of a free needle and prevents suture escape during suturing. The surgical needle enables rapid engagement and disengagement of suture by incorporating a jam cleat type mechanism.

In a first embodiment, the surgical needle includes an elongate body having a first pointed distal end and a second non-pointed proximal end defining a length. An opening (or eye) having a distal end and a proximal end is disposed at the second non-pointed proximal end of the elongate body and includes a jam cleat type mechanism.

A jam cleat is a nautical device in which a rope is pinched in a V-shaped slot. As stated above, in a first embodiment, a jam cleat type mechanism is disposed in the eye of the needle. The jam cleat squeezes suture in a V-shaped slot until it is securely wedged. The jam cleat may include a suture engaging V-shaped tapered groove having opposing side walls that meet at a jam point at the distal end of the opening. Alternatively, the jam cleat may include a suture engaging V-shaped tapered groove having opposing side walls that meet at a jam point at the proximal end of the opening. Moreover, the jam cleat may include a first suture engaging V-shaped tapered groove having opposing side walls that meet at a first jam point at the distal end of the opening and a second suture engaging V-shaped tapered groove having opposing side walls that meet at a second jam point at the proximal end of the opening.

A channel may be disposed in the elongate body for providing access from an outer portion of the elongate body to the opening at the second non-pointed proximal end of the elongate body. The channel provides an alternative means of threading suture into the opening of the elongate body.

In a second embodiment, the surgical needle includes an elongate body having a first pointed distal end and a second non-pointed proximal end defining a length. A jam cleat is disposed at the second non-pointed proximal end and includes a suture engaging V-shaped tapered groove having opposing side walls that meet at a jam point. The suture engaging V-shaped tapered groove points in a direction towards the first pointed distal end of the elongate body.

In both embodiments, the jam cleat may include a cutting means for cutting suture. For example, one (or both) of the side walls of the opposing side walls may include a sharpened edge.

In both embodiments, the elongate body of the surgical needle may be linear or curved. Moreover, the elongate body may be tapered from the second non-pointed proximal end to the first pointed distal end. All prior art surgical needle configurations, however, are envisioned.

BRIEF DESCRIPTION OF THE DRAWINGS

For a fuller understanding of the invention, reference should be made to the following detailed description, taken in connection with the accompanying drawings, in which:

FIG. 4 is a surgical needle with two jam cleats;
FIG. 5 is a surgical needle with a jam cleat and an access channel;
FIG. 6 is a surgical needle with a jam cleat and an access channel.

DETAILED DESCRIPTION OF THE PREFERRED EMBODIMENT

Figure 1:
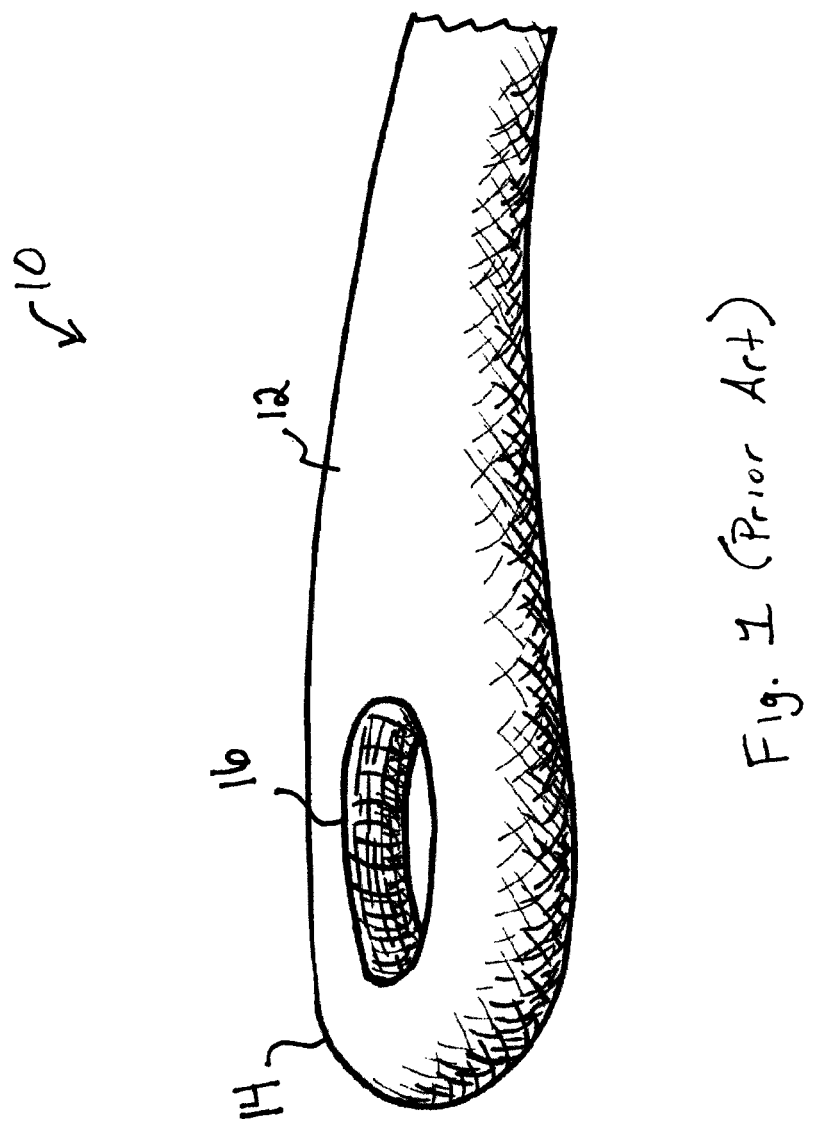
FIG. 1 is a prior art surgical needle eye.

As depicted in FIG. 1, a prior art surgical needle 10 includes an elongate body 12 having a first pointed distal end (not shown) and a second non-pointed proximal end 14 defining a length. An opening 16 (or eye) is disposed at the second non-pointed proximal end 14 of the elongate body. The opening 16 facilitates the threading of suture and is generally oval-shaped with no mechanism to lock suture in place. This enables suture to escape with little force, causing frustration for a surgeon. The claimed invention is a surgical needle including a jam cleat for preventing slippage of suture. The surgical needle enables rapid engagement and disengagement of suture by incorporating a jam cleat type mechanism.

Figure 2:
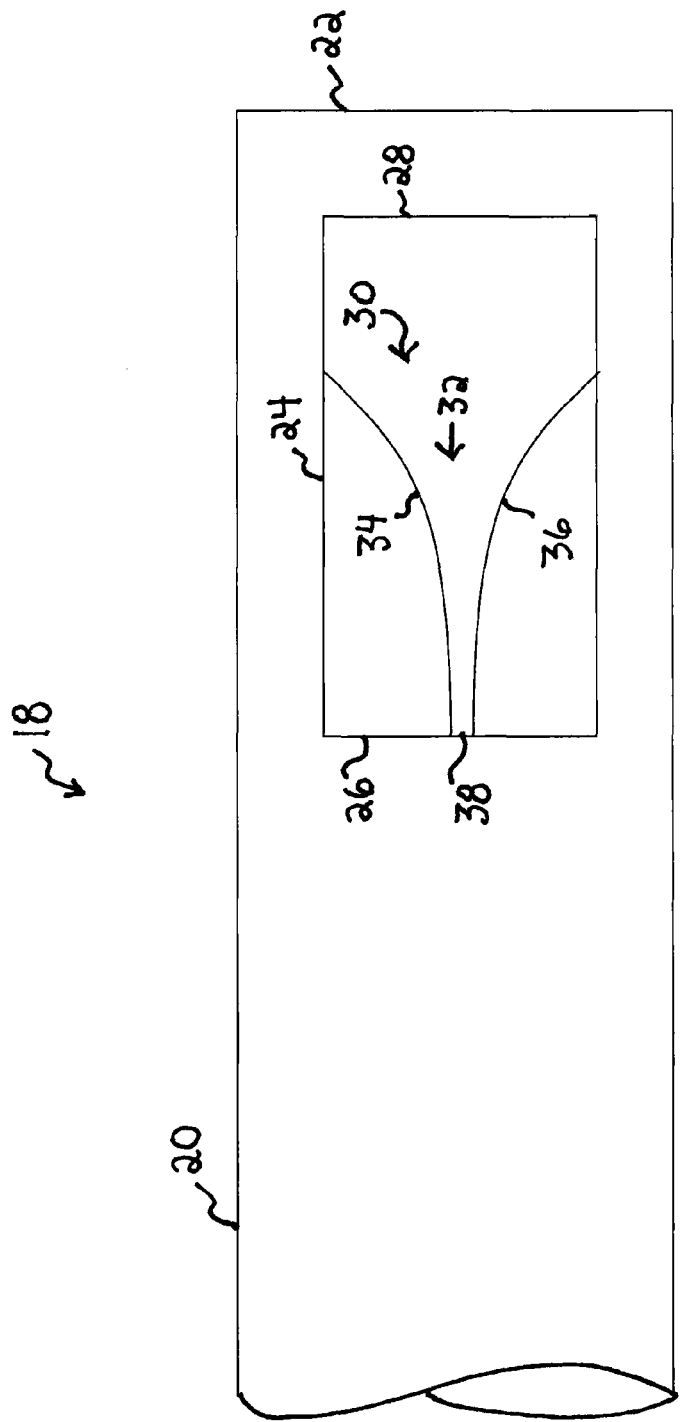
FIG. 2 is a surgical needle with a jam cleat.
Figure 3:
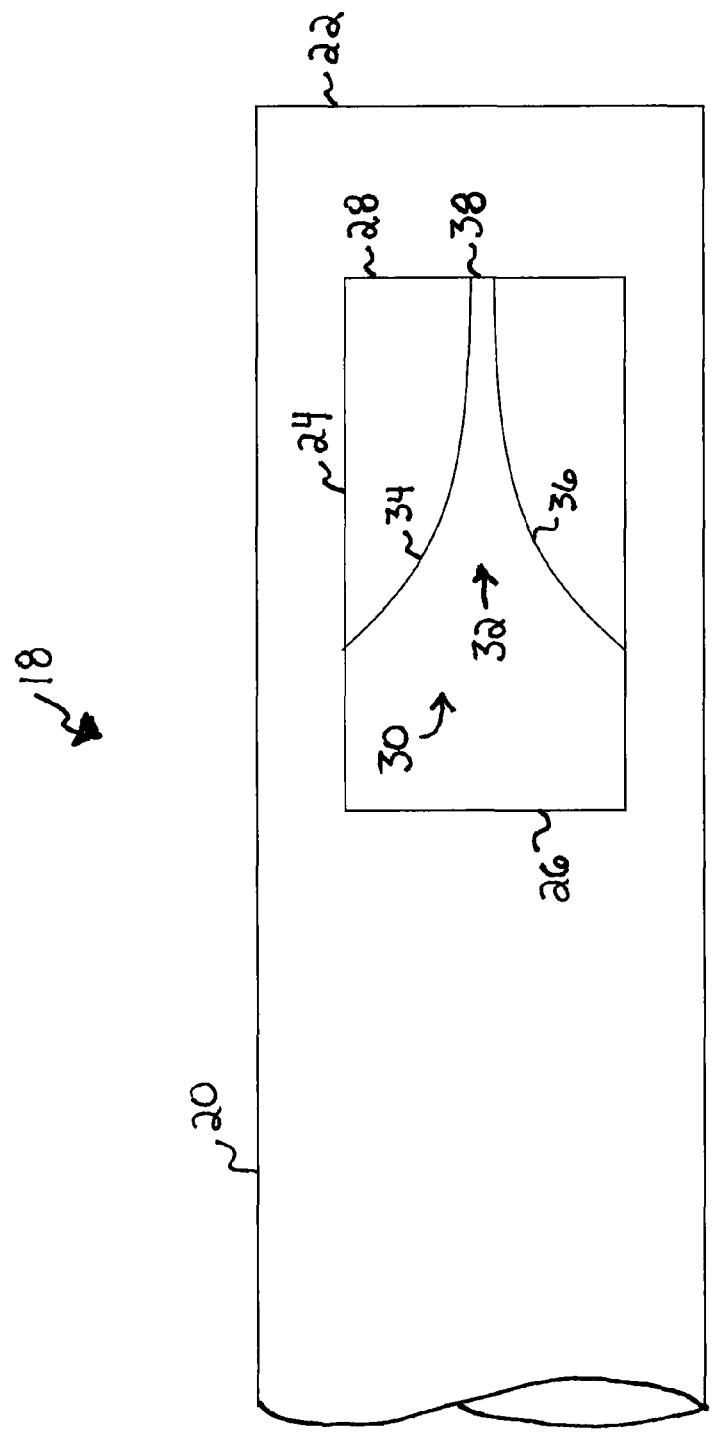
FIG. 3 is a surgical needle with a jam cleat.

In an embodiment, as depicted in FIGS. 2-4, the surgical needle 18 includes an elongate body 20 having a first pointed distal end (not shown) and a second non-pointed proximal end 22 defining a length. An opening 24 (or eye) having a distal end 26 and a proximal end 28 is disposed near the second non-pointed proximal end 22 of the elongate body 20 and includes a jam cleat type mechanism 30. The jam cleat type mechanism 30 includes a suture engaging V-shaped tapered groove 32 having opposing side walls 34, 36 that meet at a jam point 38 at the distal end 26 of the opening 24. As depicted in FIG. 3, the jam cleat type mechanism 30 includes a suture engaging V-shaped tapered groove 32 having opposing side walls 34,36 that meet at a jam point 38 at the proximal end 28 of the opening 24. As depicted in FIG. 4, the jam cleat type mechanism 30 includes a first suture engaging V-shaped tapered groove 40 having opposing side walls 42, 44 that meet at a first jam point 46 at the distal end 26 of the opening 24 and a second suture engaging V-shaped tapered groove 48 having opposing side walls 50, 52 that meet at a second jam point 54 at the proximal end 28 of the opening 24.

In use, suture is threaded through the opening and then funneled between the opposing side walls of the V-shaped tapered groove to the jam point where it is wedged securely in place. To disengage suture from the jam cleat, suture is pulled away from the jam point and then threaded out of the opening.

As depicted in FIGS. 5 and 6, a channel 56 may be disposed in the elongate body 20 for providing access from an outer portion of the elongate body 20 to the opening 24 at the second non-pointed proximal end 22 of the elongate body 20. The channel 56 provides an alternative means of threading suture into the opening 24 of the elongate body 20. Accordingly, in use, suture is passed through the channel 56 and into the opening 24. Suture is then directed between the opposing side walls 80, 82 of the V-shaped tapered groove 84 to the jam point 86 where it is secured to the needle 18. To disengage suture from the jam cleat, suture is pulled away from the jam point 86 and then directed out of the opening 24 through the channel 56.

Figure 7:
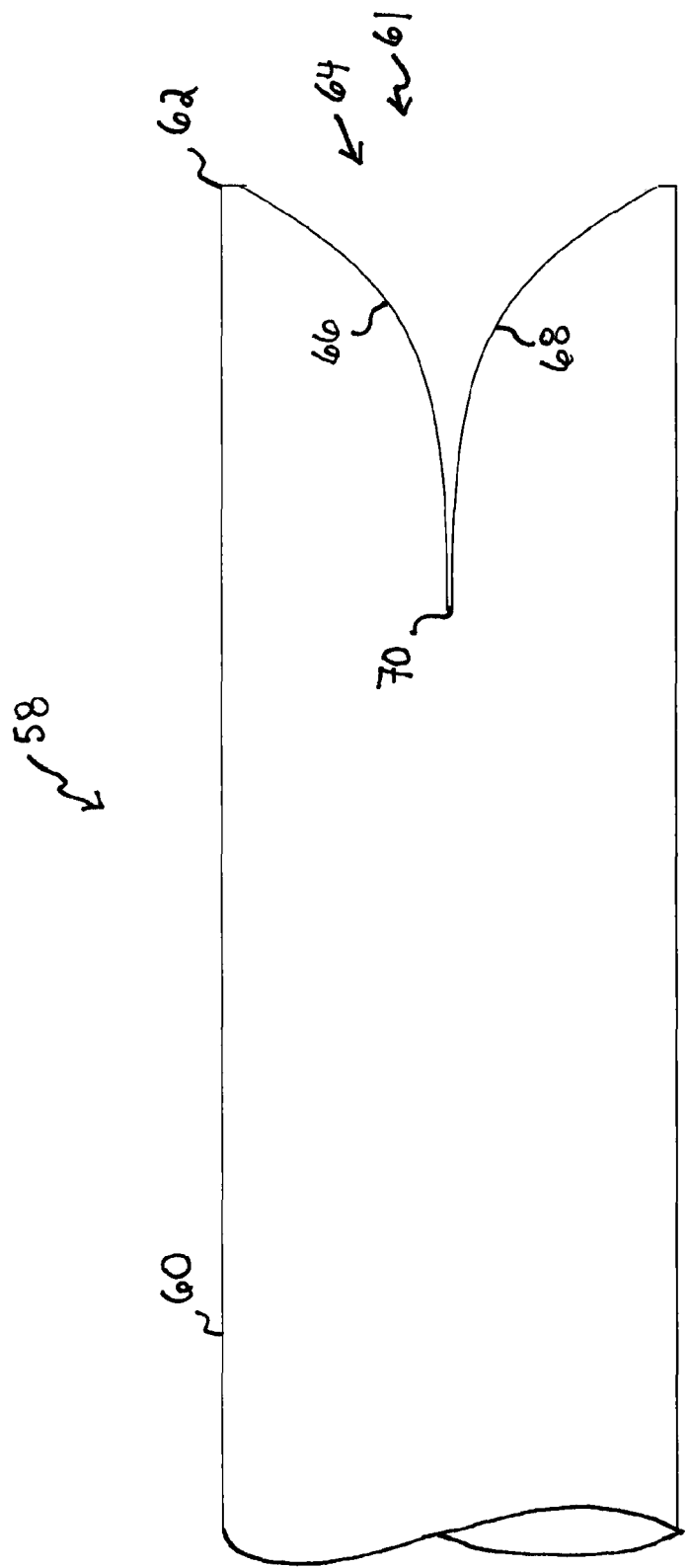
FIG. 7 is a surgical needle with a jam cleat.

In a second embodiment, as depicted in FIG. 7, the surgical needle 58 includes an elongate body 60 having a first pointed distal end (not shown) and a second non-pointed proximal end 62 defining a length. A jam cleat type mechanism 61 is disposed near the second non-pointed proximal end 62 and includes a suture engaging V-shaped tapered groove 64 having opposing side walls 66, 68 that meet at a jam point 70. The suture engaging V-shaped tapered groove 64 points in a direction towards the first pointed distal end (not shown) of the elongate body 60. Suture is funneled between the opposing side walls 66, 68 of the V-shaped tapered groove 64 to the jam point 70 where it is wedged securely in place. To disengage suture from the jam cleat type mechanism 61, suture is pulled away from the jam point 70.

In all embodiments, the jam cleat may include a cutting means for cutting suture. For example, one (or both) of the side walls of the opposing side walls may include a sharpened edge. This facilitates easier disengagement of the suture from the needle by allowing a surgeon to simply pull on suture to cut it, with the remaining fragment of suture remain clenched in the jam cleat.

Moreover, the elongate body of the surgical needle may be linear or curved or include a taper from the second non-pointed proximal end to the first pointed distal end. All prior art surgical needle configurations, however, are envisioned for all embodiment of the surgical needle having a jam cleat.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween.

What is claimed is:

1. A surgical needle for engaging a suture, comprising:
an elongate body having a first pointed distal end and a second non-pointed proximal end defining a length; and
a jam cleat disposed at said second non-pointed proximal end, said jam cleat including a suture engaging V-shaped tapered groove having opposing side walls that meet at a jam point, such that the suture is securely wedged between said opposing side walls into said jam point;
said suture engaging V-shaped tapered groove pointing in a direction towards said first pointed distal end;
said jam cleat positioned within an opening disposed at said second non-pointed proximal end of said elongate body;
said jam point positioned at a distal end of said opening; and
said jam cleat further including an additional suture engaging V-shaped tapered groove having opposing side walls that meet at a second jam point, said additional suture engaging V-shaped tapered groove pointing in a direction towards said second non-pointed proximal end, said second jam point positioned at a proximal end of said opening.

2. A surgical needle as in claim 1, further comprising:
said elongate body being curved.

3. A surgical needle as in claim 1, further comprising:
said elongate body being tapered from said second non-pointed proximal end to said first pointed distal end.

4. A surgical needle as in claim 1, further comprising:
said jam point positioned at a distal end of said opening.

5. A surgical needle as in claim 1, further comprising:
said jam cleat including a cutting means for cutting said suture.

\* \* \* \* \*